Figures 1, 2:
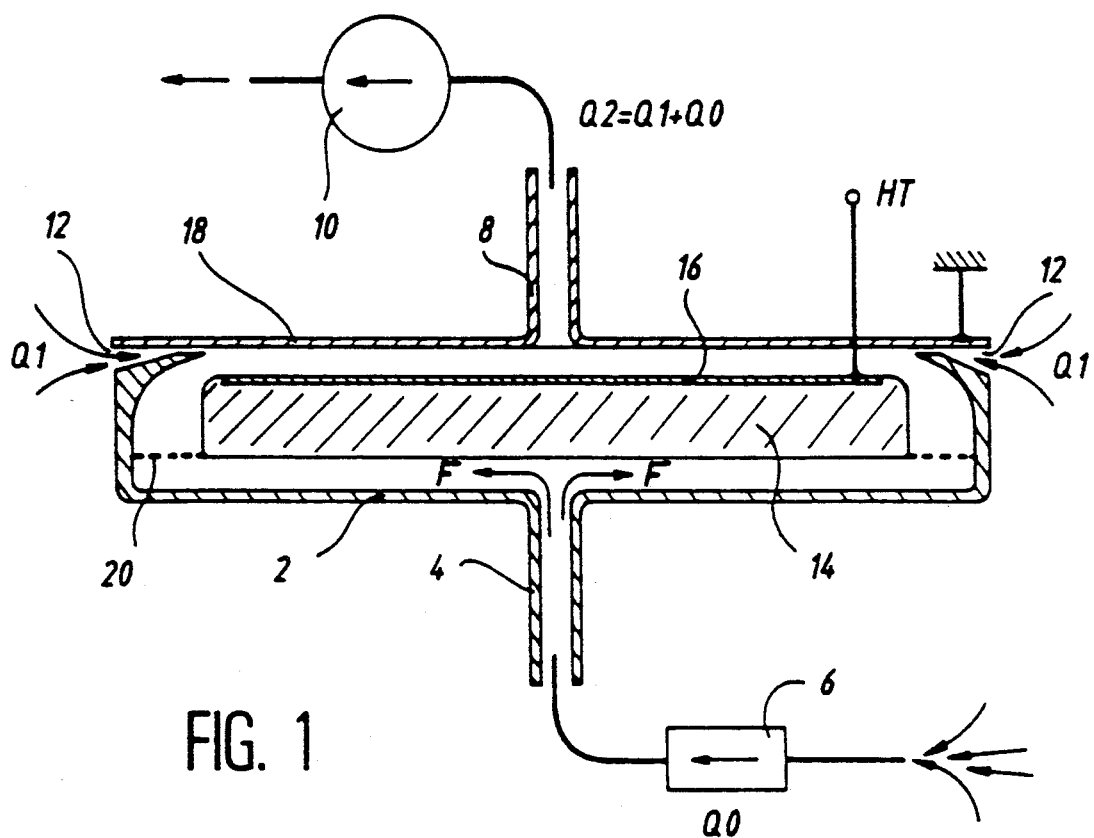

United States Patent [19]
Pourprix

[11] Patent Number: 5,117,190
[45] Date of Patent: May 26, 1992

[54] ELECTROSTATIC DETECTOR OF AEROSOL PARTICLES

[75] Inventor: Michel Pourprix, Montlhery, France

[73] Assignee: Commissariat a L'Energie Atomique, Paris, France

[21] Appl. No.: 542,030

[22] Filed: Jun. 22, 1990

[30] Foreign Application Priority Data

Jun. 23, 1989 [FR] France .................. 89 08400
Feb. 27, 1990 [FR] France .................. 90 02413

[51] Int. Cl.$^5$ .......................................... G01N 27/60
[52] U.S. Cl. ........................................ 324/452; 324/457
[58] Field of Search ............... 324/452, 453, 457, 464

[56] References Cited

U.S. PATENT DOCUMENTS

| | | | |
|---|---|---|---|
| 3,566,107 | 2/1971 | Taylor et al. | 324/465 X |
| 4,117,715 | 10/1978 | Hoenig | 324/452 X |
| 4,387,369 | 6/1983 | Klein et al. | 324/464 X |
| 4,556,849 | 12/1985 | Kalakutsky et al. | 324/464 |

FOREIGN PATENT DOCUMENTS

| | | | |
|---|---|---|---|
| 2843246 | 4/1980 | Fed. Rep. of Germany | 324/453 |
| 657372 | 4/1979 | U.S.S.R. | 324/452 |
| 1533113 | 11/1978 | United Kingdom . | |

OTHER PUBLICATIONS

Schowengerdt et al, "A Parallel-Plate Electrostatic Size Classifier for Aerosol Particles" *Rev. Sci. Instrum.* 51(8) Aug. 1980, pp. 1098-1104.
O. G. Raabe, "Instruments and methods for characterizing radioactive aerosols", IEEE Nuclear Science, vol. NS-19, Feb. 1972, pp. 64-75.

*Primary Examiner*—Kenneth A. Wieder
*Attorney, Agent, or Firm*—Spensley Horn Jubas & Lubitz

[57] ABSTRACT

Electrostatic detector according to claim 2, characterized in that it is constituted by a flattened circular cylindrical case (2) having two axial pipes, one for injecting a gas (4) into the lower part of the case and the other for extracting the gas (8) in the upper part of said case, the latter being provided on its upper periphery with an annular slot (12) for the entry of the atmosphere to be analyzed and, in its center, a solid thick disk (14), whose upper face supports one of the two conductive disks (16), the second conductive disk (18) being constituted by the upper cover of the case, the injection gas flow passing round the thick disk after passing through a filter (20) for the purification and uniform distribution of its flow.

15 Claims, 6 Drawing Sheets

ELECTROSTATIC DETECTOR OF AEROSOL PARTICLES

The present invention relates in general terms to the field of the electrostatic detecting, collecting or sensing of aerosol particles with a view to their study, more particularly under the angle of their mobility or their electric charge, as well as the collection thereof for subjecting them to analysis systems.

In general terms it is pointed out that the term aerosol is used for suspensions of particles of solid or liquid matter in a gaseous phase, the size of said particles varying considerably. The finest particles correspond to molecular aggregates of a few dozen Angstroms, whilst the largest particles, normally resulting from mechanical actions, can have a size of about 100 micrometers. Microorganisms, viruses, bacteria and pollens are also considered to be aerosol particles and, when suspended in a gas, have a behaviour identical to that of other inert particle types. A by no means negligible aerosol category is constituted by radioactive aerosols, whose origin can be certain radioactive gases, such as e.g. the descendants of radon or particles resulting from the dispersion in the atmosphere of pulverulent products from the nuclear industry.

Numerous reasons, quite independent of the scientific study of phenomena, make it particularly interesting to study, detect and measure aerosols. Reference can be made to their action on the quality of the environment in the natural medium, their action on living beings and on man and in particular when they are inhaled by the respiratory tracts, as well as the contamination which they can cause on certain fabricated products, particularly in the agroalimentary and pharmaceutical fields and now in laboratories or factories for producing semiconductor components, where working takes place in very high purity atmospheres, known as white rooms.

One of the most frequently used means for detecting and measuring aerosols is based on the fact that they are substantially all carriers of electric charges, equal to the unit or multiple electric charge thereof. It is pointed out that in general terms in a given volume of atmosphere, the sum of the positive and negative electric charges carried by the particles of an aerosol is zero. This means that at all times, the sample contained in said atmosphere part has the same number of positive as negative charges and generally in accordance with a Gaussian distribution centred on the zero charge and decreasing as a function of the number of elementary charges.

Thus, for the detection of the presence, the sampling and the measuring of aerosols, use has frequently been made of electrostatic fields acting on the electric charges which they carry. For this purpose, a fundamental notion in this field is that of the electric mobility of a charged particle placed in an electrostatic field. This quantity, which defines the aptitude of a particular particle to undergo a deflection under the effect of said field can be represented by the following equation:

$$\vec{W} = Z\vec{E}.$$

In said vector equation $\vec{W}$ is the speed of the drift acquired by the particle under the influence of the electric filed $E$ to which it is subjected. The proportionality coefficient $Z$ between the two preceding quantities is precisely the electric mobility in question. In accordance with intuition, said electric mobility is proportional to the electric charge of the particle and inversely proportional to its grain size distribution, so that it is possible to produce true electric mobility spectrometers consisting of subjecting the aerosol particles entrained in a gas flow to the action of an electric field existing between two electrodes. Under the effect of the field, the particles charged with these aerosols are deposited, as a function of their sign, on one of the said electrodes and the abscissa of their deposit with respect to the gas flow direction characterizes their mobility in the sense that the greater the said electric mobility, the closer the abscissa of their deposit is to the origin of the gas flow carrying them. Thus, there is a spreading in space of the collected particles effecting a spectrometry thereof as a function of their electric mobility.

Hitherto apparatuses of this type have operated with structures having cylindrical or parallelepipedic geometry flow forms. These known structures suffer from two serious deficiencies, namely a certain production problem and when the collecting electrode is cylindrical it is relatively difficult to examine the particles precipitated therein and secondly in order to obtain a good quality electric mobility spectrometry, the flow of the gas carrying the aerosol particles must be of high quality both as regards its laminar flow characteristics and its stable flow characteristics. This is not generally the case in the hitherto used cylindrical and/or parallelepipedic structures.

The present invention relates to an electrostatic detector, collector or sensor of aerosol particles, whose production and exploitation by subsequent measuring equipment is much simpler than in the aforementioned existing structures and which also offers the major advantage of permitting a carrier gas flow as a perfect and stable laminar flow.

This electrostatic detector of aerosol particles contained in an atmosphere to be examined is characterized in that it comprises two spaced, parallel, coaxial conductive disks between which is established an electric field by raising them to different potentials, the space between the two disks communicating over its entire periphery with the atmosphere to be examined, a central suction being provided in said space in order to bring about the circulation therein, from the periphery of the disks, of part of said atmosphere in the form of a stable, centripetal, laminar flow.

The essential and novel feature of the electrostatic detector according to the invention is consequently that it works with two disk-shaped electrodes and has a flow of the atmosphere to be examined between said two disks in the form of a stable, centripetal, laminar flow from the periphery to the centre of the apparatus where the flow is sucked in. This gives an easily manufacturable apparatus, because the conductive disks can be produced very easily. Moreover, the particle fixing electrodes lend themselves very well to analysis, e.g. by a spectrometre, because the particles are distributed in concentric zones, whose electric mobility decreases from the periphery to the centre. In addition, the structure having a circular symmetry, allows a perfectly stable, controlled, laminar flow.

According to a very interesting embodiment according to the invention, the electrostatic detector is characterized in that the flow rate of the atmosphere to be examined is the differential resultant of the central suction flow rate and a filtered gas peripheral injection flow rate, the latter being regulated to a value below that of the suction flow rate. This embodiment is particularly appropriate for a precise determination of the value of the flow rate of the atmosphere to be examined, because the latter results, by definition, from the perfectly controlled difference between the sucked gas flow rate and the injected filtered gas flow rate.

According to the invention, it is also advantageous to construct the electrostatic detector with the aid of a flattened, circular, cylindrical case having two axial pipes, one for injecting the gas in the lower part of the case and the other for the extraction of the gas in the upper part of the case, the latter being provided on its upper periphery with an annular slot for the entry of the atmosphere to be analyzed and, in its centre, with a solid, thick disk, whose upper face supports one of the two conductive disk, the second conductive disk being constituted by the upper cover of the case, the injection gas flow passing round the thick disk after passing through a filter for the purification and uniform distribution of its flow.

According to the invention and as a function of the sought results, for the application of the electrostatic detector to the production of an aerosol particle electric mobility spectrometer, different parameters exist which are the intensity of the electric field between the two disks and the radial, laminar flow rate of the atmospheric sample to be examined. As a function of the value imposed on these different parameters, a fixing is obtained of all or part of the dispersed particles in the form of concentric, annular zones on disks constituting the two electrodes, whereby the mobility spectrum can be deduced by a calculation or a data processing on the basis of the examination of the location of said annular zones, their density and the grain size distribution of the particles.

Obviously and as in the prior art electrostatic detectors, it is of interest, if it is wished to be certain to detect all the particles constituting a given aerosol, to subject them during their entry into the apparatus to fixing means with respect to said particles of electric charges of the same sign. This can be carried out in different ways and namely by placing at the entry of the gaseous flow of an annular chamber containing a radioactive, ionizing source associated with a polarization grid in order to separate the charges having a given sign, or an annular chamber provided with charged microdots in order to bring about the ionization of the gas by the corona effect.

In a special embodiment, one of the collecting disks can be made from a material emitting ionizing radiation.

However, if in a particular case, it is wished to collect and analyze even the neutral aerosol particles, it is possible to add to the gas extraction device a static filter, which will hold back said neutral particles.

An interesting embodiment of the electrostatic detector according to the invention consists of placing in the case constituting the same, a certain number of sector-type, peripheral electrodes, each provided with an electric supply. It is therefore possible to raise them to an adequate potential for trapping all the particles entering the corresponding sector and consequently the detector can be operated by sequential sectors.

Another application of the electrostatic detector according to the invention is the construction of an aerosol particle electric mobility selector, characterized in that at least one of the two coaxial conductive disks is provided with an annular slot centred on the axis common to both disks, in conjunction with means for sucking, through said slot, particles which would normally be deposited on the disk at the location of said slot if it did not exist.

According to a variant of said mobility selector, the suction means consist of a cylindrical case, joined to one of the disks and containing the slot, and which is provided with a suction tube to permit the selective extraction of the particles having the electric mobility corresponding to the radius of the slot.

Another application of the electrostatic detector according to the invention is the construction of a device for obtaining a homogeneous surface deposit standard of particles on a disk-like substrate.

The said apparatus is characterized in that the electrostatic detector, whose substrate constitutes one of the conductive disks, is supplied by an aerosol particle flow having in common the same value for two out of the three quantities constituted by the electric mobility, the charge and the size and in that the potential difference V between the disks of the detector is varied as a function of time during the deposit and in accordance with the law:

$$V = \frac{2h}{Z\left(\frac{\pi r_A^2}{Q} - \frac{N}{S}t\right)}$$

in which:
h is the half-distance between the plates,
Z is the electric mobility common to the particles,
rA is the distance from the aerosol injection point to the detector axis,
Q is the extraction flow rate of the gaseous phase from the detector,
N is the concentration of particles in the extraction flow rate Q, when V=0,
S is the surface density of the particles which it is wished to obtain on the collecting disk,
t is time.

Another application of the electrostatic detector according to the invention is the production of a total collection electrostatic detector able to select all the aerosols having a grain size distribution below a given threshold, characterized in that it comprises, on the introduction path of the gaseous phase containing the aerosols, a calibrated annular slot for bringing about, for an appropriate extraction flow rate, the inertial separation of the particles having a grain size below the threshold and the deposition of said particles on a collecting disk.

The invention is described in greater detail hereinafter relative to non-limitative embodiments and the attached drawings, wherein show:

FIG. 1 In section, along the axis of an electrostatic detector according to the invention in its most general constructional embodiment.

FIG. 2 A plan view showing the dispersion state of the particles of an aerosol, after fixing to the collecting electrode of the means according to FIG. 1.

FIG. 3 An interesting application of the detector according to the invention, in which the collecting electrode and its support are constituted by a Petri dish, used in biology for collecting bacterial aerosols.

FIG. 4 An embodiment of the electrostatic detector according to the invention making it possible, when desired, to simultaneously collect positively and negatively charged particles of the same aerosol.

Figure 5:
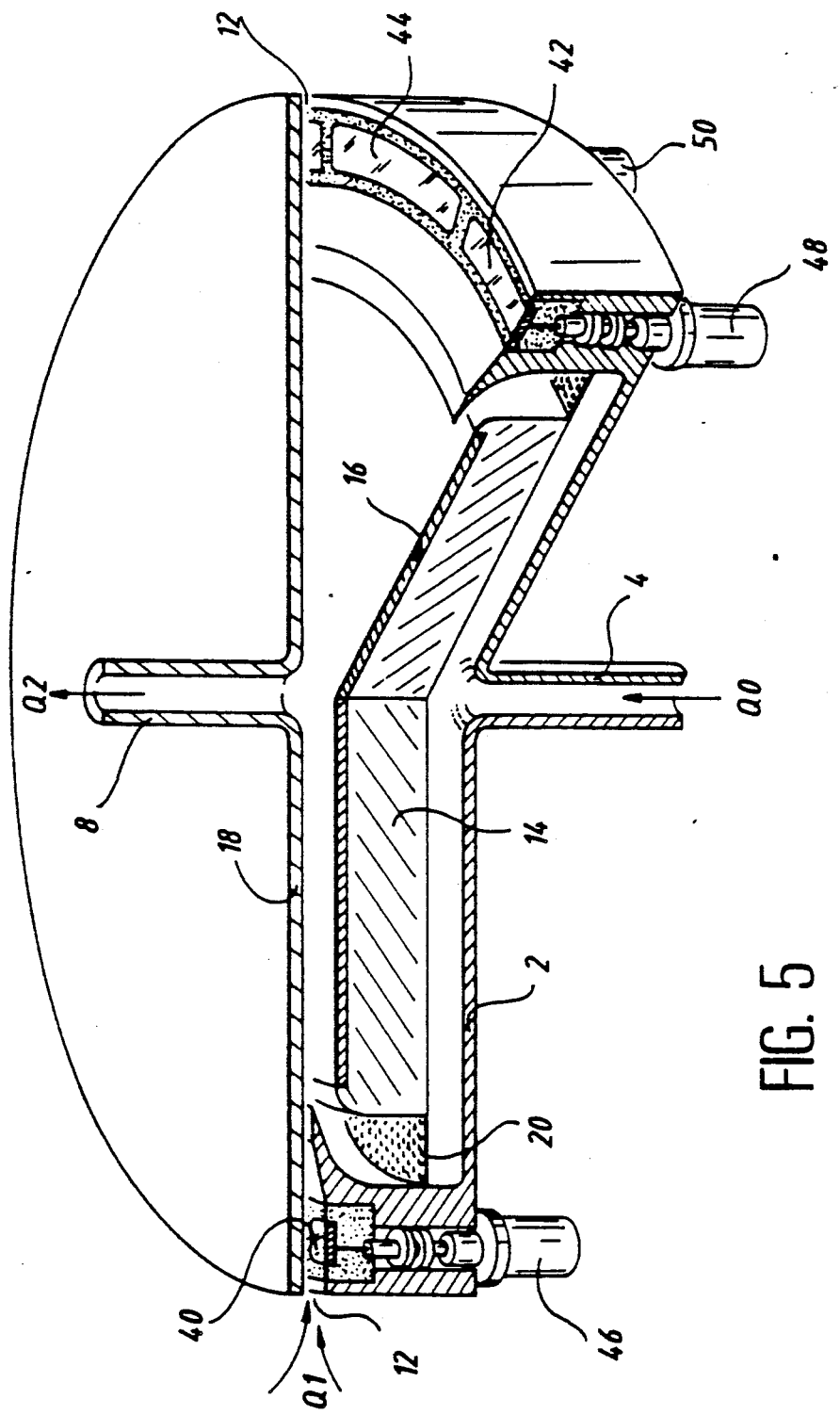

FIG. 5 An embodiment of the detector of FIG. 1 able to operate on successive sequential sectors.

Figure 6:
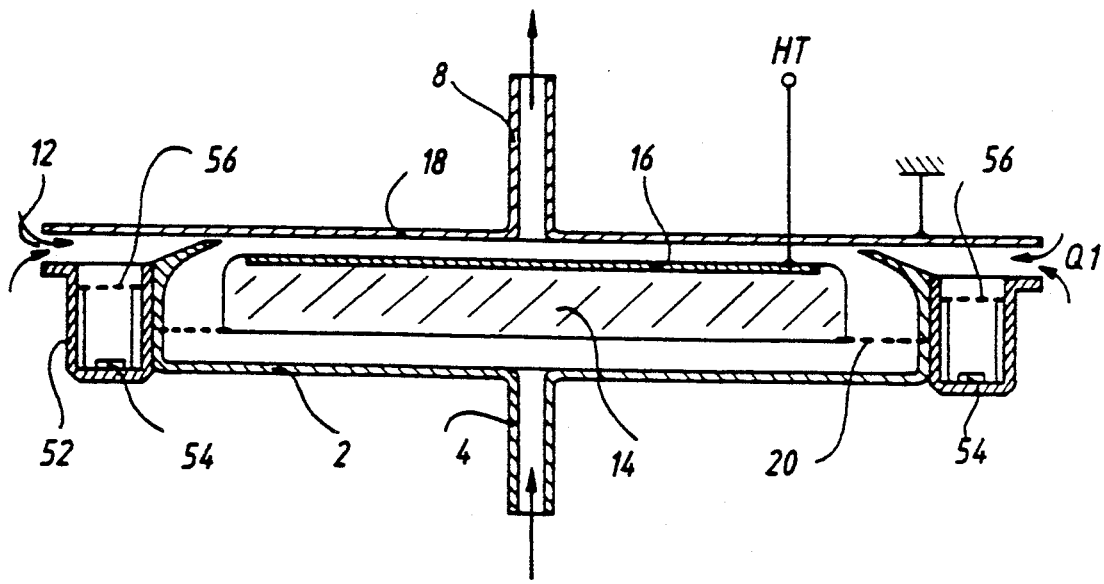

FIG. 6 An embodiment of the detector of FIG. 1 equipped with means for charging the particles of aerosols analyzed prior to their entry into the apparatus.

Figure 7:
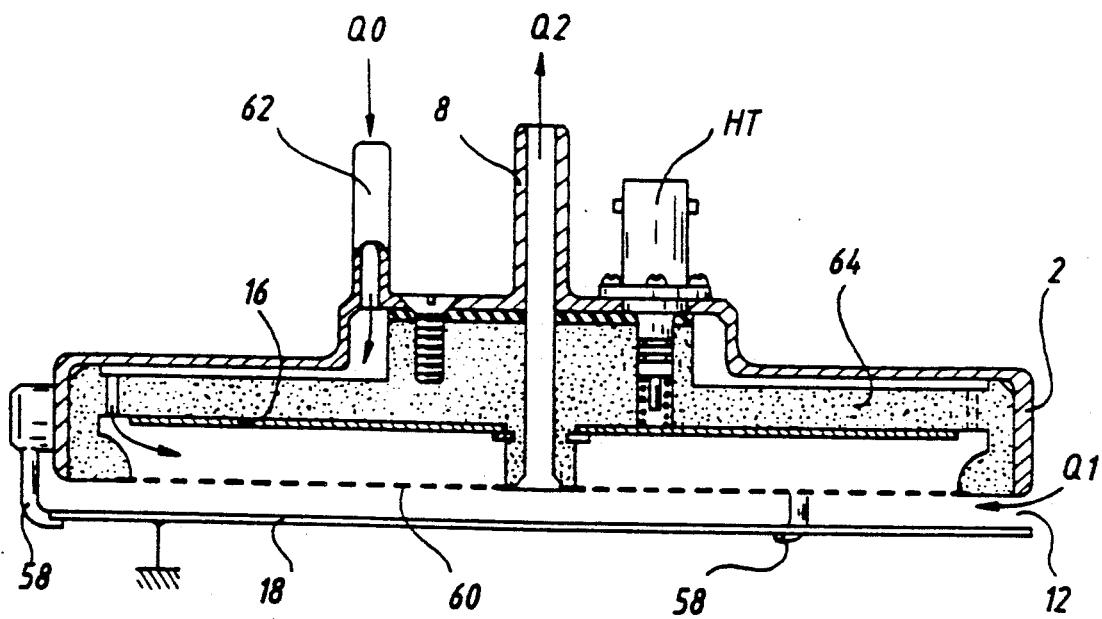

FIG. 7 An embodiment of the electrostatic detector according to the invention, in which one of the two conducting disks serving as the electrode itself emits ionizing particles.

Figure 8:
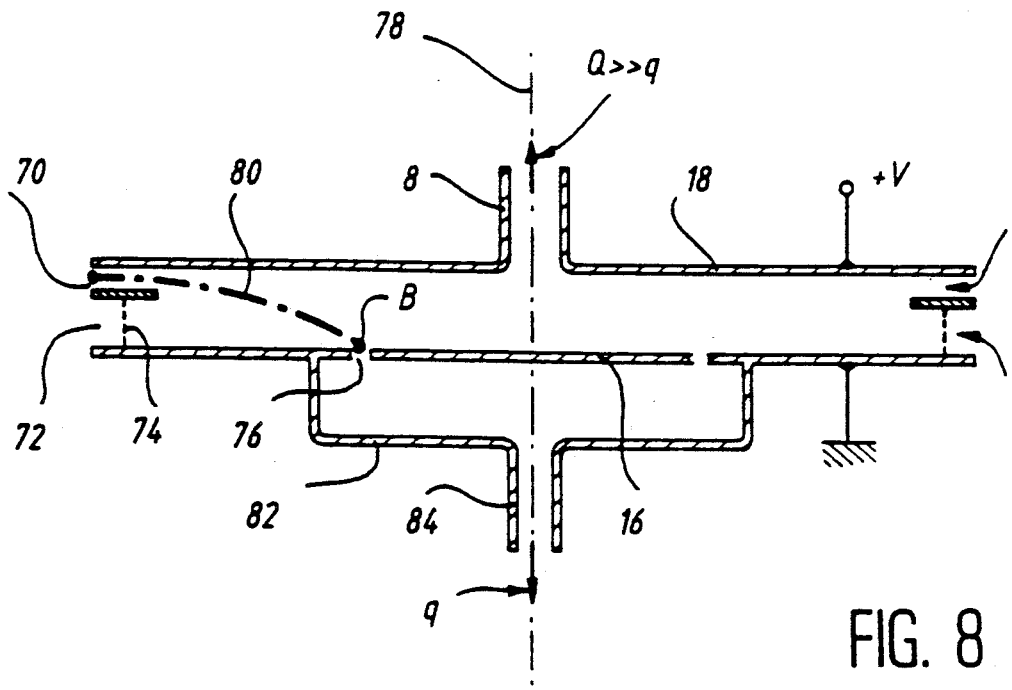

FIG. 8 The diagrammatic principle for producing an electric mobility selector of particles of an aerosol according to the invention.

Figure 9:
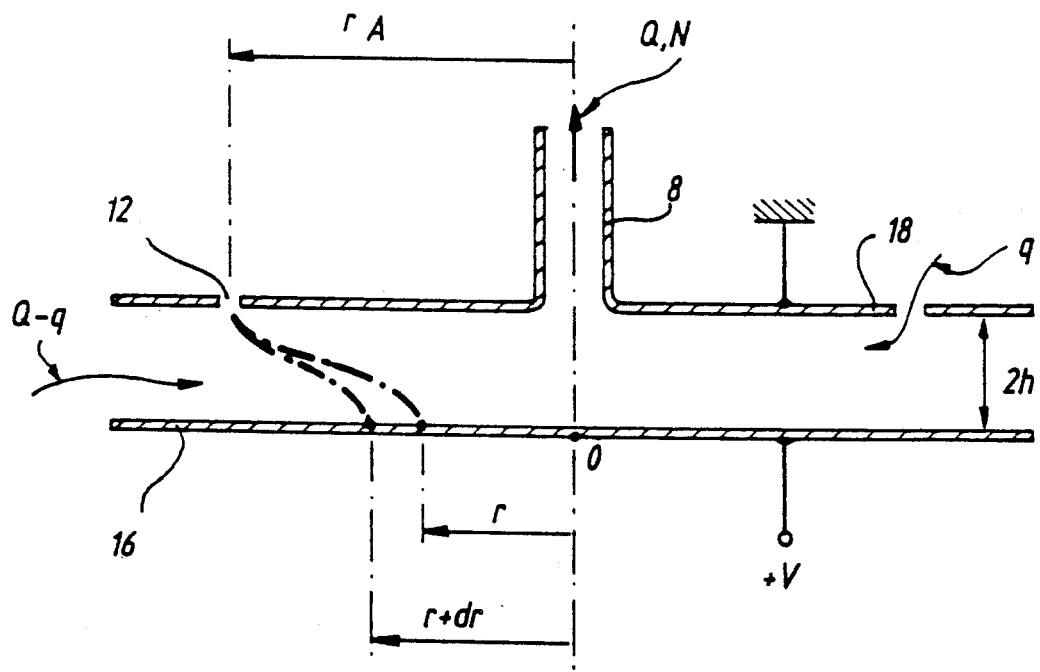

FIG. 9 A diagram explaining the dispersion of the deposits of particles on the collecting plate of an electrostatic detector.

Figure 10:
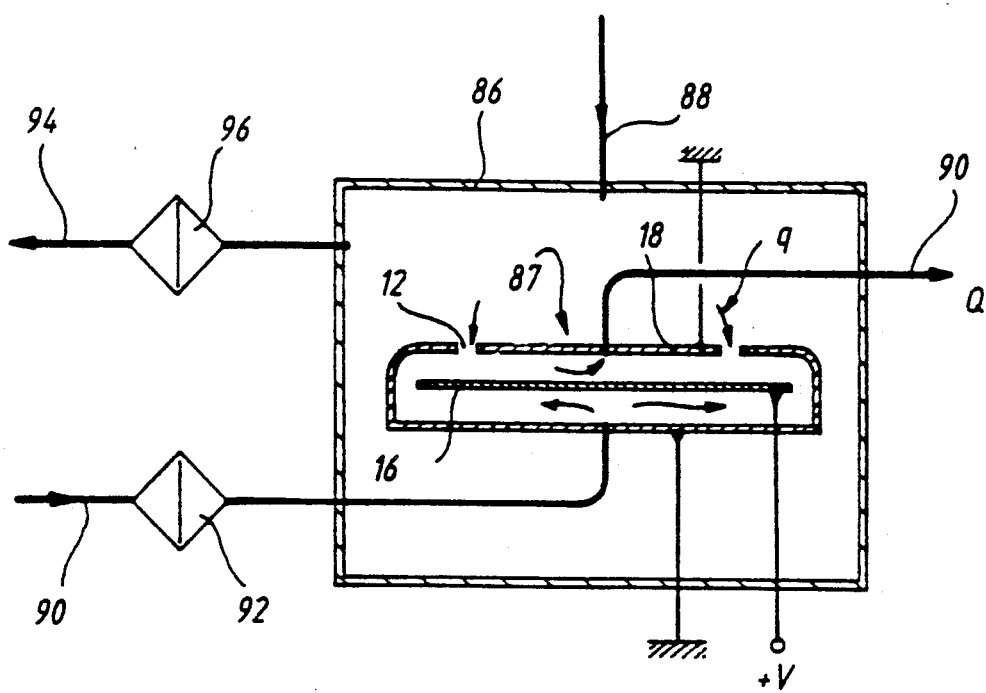

FIG. 10 A simplified diagram of an apparatus for obtaining a standard surface deposit of particles on a substrate.

Figure 11:
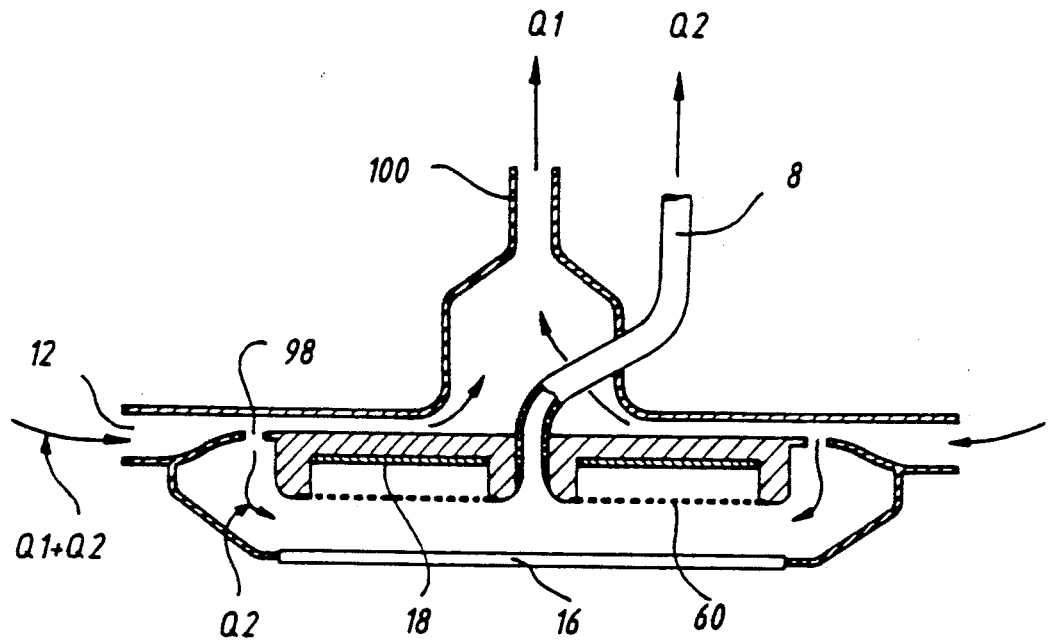

FIG. 11 A diagrammatic exemplified embodiment of an electrostatic collector with total collection according to the invention.

FIG. 1 shows the most general and simplest embodiment of the aerosol electrostatic detector according to the invention. The detector essentially comprises, in a flattened, circular, cylindrical case 2, equipped along its central axis with an inlet 4 for the injection flow rate $Q_o$ of atmospheric entrainment air under the effect of a pump 6. Along the same axis, but at a higher level is provided a discharge pipe 8 for the atmosphere sucked in under the effect of the suction pump 10. In the upper part of the case 2 is provided an annular slot 12 for the penetration of the atmosphere to be examined under the angle of its aerosol particle content. The sampling flow rate $Q1$ of the air to be examined for making it flow in the case 2 results from the difference between the air suction flow rate $Q2$ under the effect of the pump 10 and the injection flow rate $Q_o$ at the entry under the effect of the pump 6.

Within the case 2 is located a solid thick disk 14, which may or may not conduct electricity and on whose upper surface rests one of the two coaxial, conductive disks 16 which, with the upper part 18 of the case 2, constitute the two coaxial conductive disks characterizing the invention. The upper disk 18 is connected to earth or ground, whereas the lower disk 16 is raised to a high positive or negative voltage compared to the same earth or ground. The atmospheric air sampled by the pump 6 and injected into the pipe 4 enters the case 2 by the lower part and is distributed therein according to a revolution of symmetry symbolized by the arrows F for traversing an annular filter 20, which completely purifies it eliminating all the suspended particles contained therein and whilst regularizing its flow. Once the said air has been filtered it passes round the upper part of the thick disk 14 and entrains the atmospheric flow rate $Q1$ to be examined in accordance with a stable, centripetal laminar flow in the space between the two coaxial, conductive disks 16 and 18. This air is then sucked to the centre of the apparatus by pipe 8 under the effect of the pump 10. Following a certain operating time necessary for the electrostatic detecting or collecting on the disks 16 and 18 of the aerosol particles contained in the atmospheric flow sampled through the opening 12, it is possible to open the apparatus and observe the disk 16, which has the appearance shown in FIG. 2 where, by means of points which are at a varying distance from one another, are shown the different concentric, annular, fixing zones dispersed in accordance with the radii of the disk 16 for the aerosol particles fixed at distances from the centre of the disk 16, which are a function of their electric mobility, their grain size distribution and their electric charge.

In the apparatus according to FIG. 1, the disk 16 or collection support can be in general terms a random metal disk to which is applied the high voltage, but in a particularly interesting case it can be a silicon wafer such as are used in the white rooms of the microelectronics industry. The detailed examination of the distribution and grain sizes of the different particles on the disk 16, as shown in FIG. 2, permits with the aid of a surface deposit analyzer and data processing to randomly determine the charge state of the different particles suspended in the examined atmosphere. This is of interest for the white rooms of the microelectronics industry, where it is known that said charge state of the particles directly conditions their aptitude for fixing to the silicon wafers used as a substrate in microelectronics.

Moreover, through the use of a silicon wafer as the collection support 16, a number of different advantages are obtained, such as e.g. the possibility of using on starting up a collection support 16, whose surface contamination level is guaranteed to be extremely low, e.g. with less than five particles with a grain size above 0.5 micrometer over the entire surface.

In addition, extremely high performance analysis systems which have recently been marketed make it possible to determine the size of the particles deposited on such a silicon wafer with extreme accuracy between 0.1 and 10 micrometers, as well as the number thereof in each grain size class.

On the basis of the thus acquired knowledge regarding the number and grain size distribution of the aerosol particles deposited on an annular surface between the radii $r$ and $r+r$, as well as the knowledge of the electric mobility directly linked with the impact location of the particles, it is possible to deduce their distribution spectrum from electric charges. This quantity is of particular interest for preventing atmospheric pollution in the white rooms of the micro-electronics industry.

Figure 3:
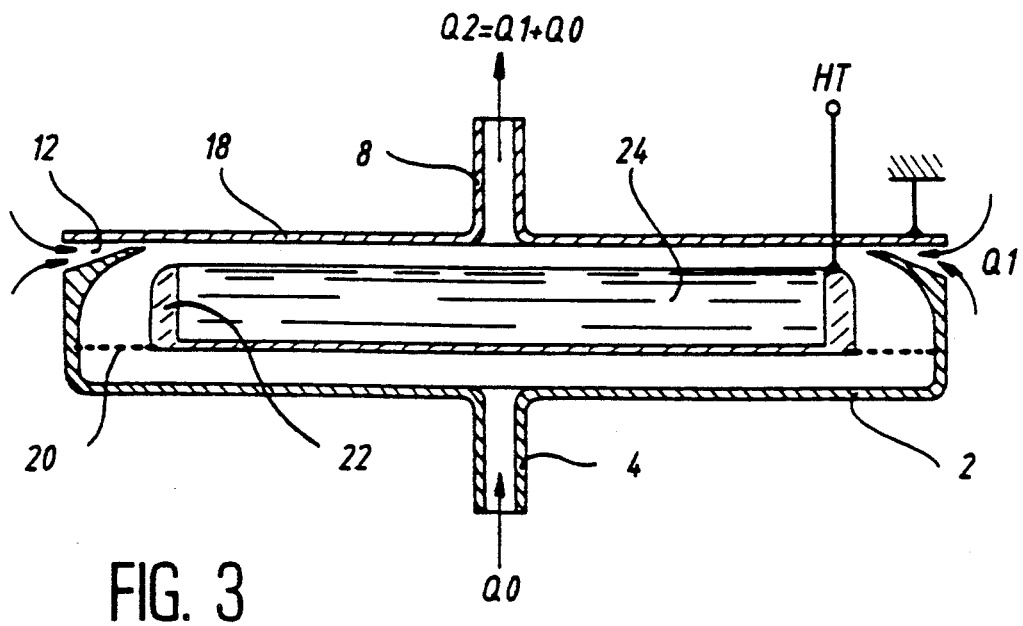

In the embodiment of the electrostatic detector according to the invention shown in FIG. 3 is shown an application more particularly directed at the identification of the spectrum of bacteria contained in an atmospheric sample to be analyzed. To this end, the apparatus according to FIG. 3, where it is possible to see the same elements as in FIG. 1 and carrying the same reference numerals, has in place of the solid, thick disk 14 a Petri dish 22 filled with an electrically conductive, gelatinous culture medium 24. During the operation of the detector according to the same principle as that described relative to FIG. 1, the bacteria contained in the atmosphere sampled through the annular opening 12 are deposited on the surface of the gelatin 24, where they are fixed and where it is consequently possible to reveal and examine them, e.g. with the naked eye or with an image analyzer, following the development of the culture seeded in this way in a location having an appropriate temperature. This easily gives the electric mobility of the bacteria contained in the sampled air.

In this example, like that of FIG. 1, the filter 20 located on the path of the entrainment air injected into the pump 6 has the double function of holding back the aerosol particles contained in the entrainment air in such a way that the latter penetrates the space between the two disks 16 and 18 in a perfectly pure state and also of homogenizing the gaseous streams, thereby participating in the preparation conditions for a perfectly stable, centripetal, laminar flow.

Obviously, the particles collected in the apparatus of FIG. 1, or the bacteria fixed therein in FIG. 3, correspond to those carrying electric charges of opposite sign to that of the polarization of the electrode 16 of FIG. 1 or the Petri dish 22 of FIG. 3. Thus, by changing the sign of said high voltage polarization, it is possible to collect particles and/or bacteria having positive or negative electric charges.

In both FIGS. 3 and 1, the experimenter has two parameters, namely the flow rates $Q_o$ and $Q2$ on the one hand and the value of the high voltage applied to the conductor 16 or the Petri dish 22 on the other for choosing the range of the spectrum of the particles or the bacteria which it is wished to fix for subsequent study purposes.

Figure 4:
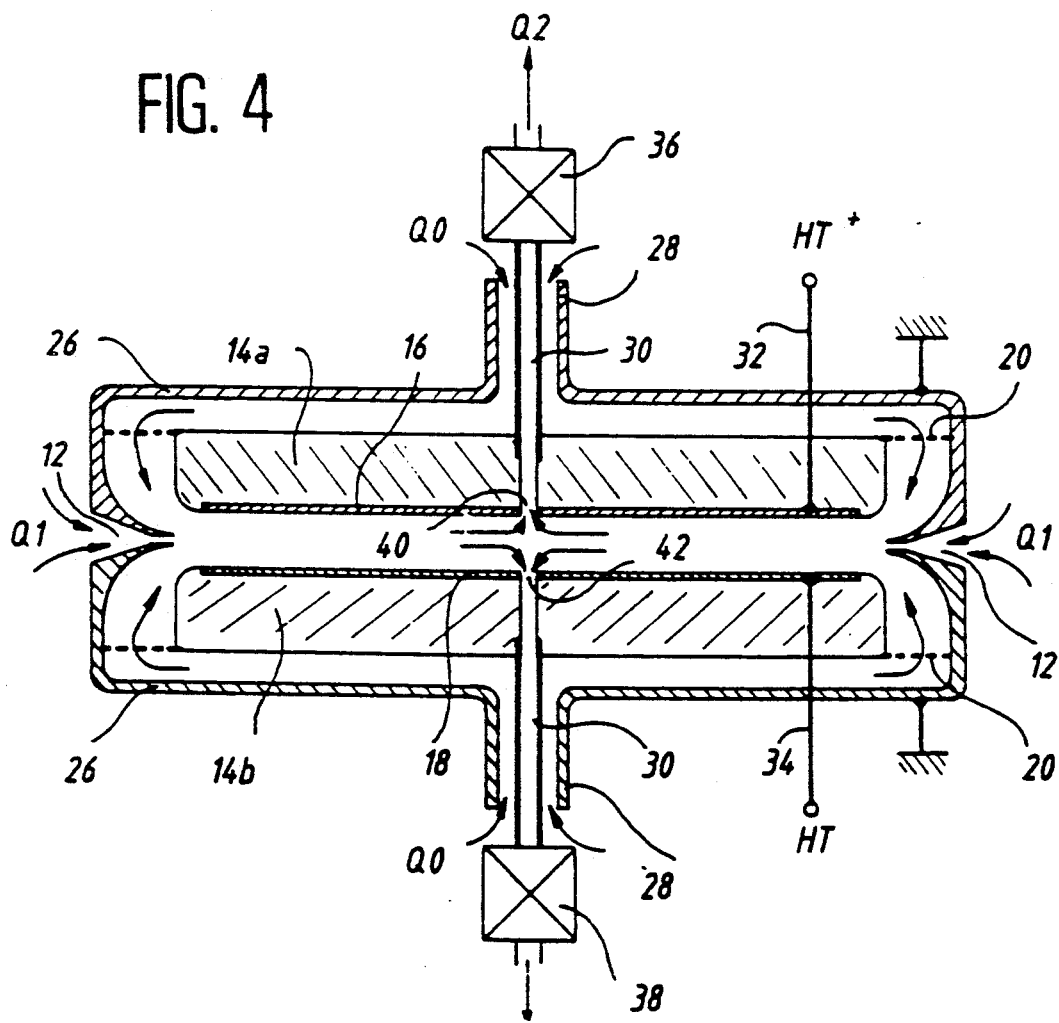

FIG. 4 shows an embodiment of the electrostatic detector for collecting aerosol particles which are both positively and negatively charged. This embodiment essentially comprises a circular, cylindrical case 26 having in its diametral plane of symmetry the annular peripheral opening 12 through which is sucked the flow rate Q1 of the atmosphere to be analyzed. Along its circular axis of symmetry, the cylindrical case 26 is provided on both its upper and lower parts with two concentric pipes, namely an external pipe 28 for the injection of the flow $Q_o$ and in its internal part with a second concentric pipe 30 for the suction of the flow Q2 under the effect of not shown pumps.

In this embodiment, the two conductive disks 16 and 18 for the collection of the charged particles are positioned facing one another and symmetrically on either side of the diametral plane of symmetry of the case 26. As in the example of FIG. 1, they are carried by thick, solid disks 14a and 14b. The case 26 is earthed or grounded and each of the two conductive disks 16 and 18 is raised by a conductor such as 32 for the disk 16 and 34 for the disk 18 respectively to a high positive and negative voltage symmetrical with respect to the earth or ground, so as to collect on the conductive disk 16 negatively charged aerosol particles and on the conductive disk 18 positively charged aerosol particles.

If, for particular reasons, it is also wished to complete the collection of charged particles by neutral particles, in the manner shown in FIG. 4, two passive mechanical filters 36 and 38 are placed on the suction outlets of the two pipes 30.

The suction of the stable, centripetal, radial flow from the peripheral, annular openings 12 takes place through orifices 40 and 42 respectively located at the central point of the conductive disks 16 and 18 and via which the gaseous streams of the radial, laminar flow pass to the outside.

FIG. 5 shows an improved embodiment of the electrostatic detector according to FIG. 1, in which the peripheral part of the case 2 is provided with planar electrodes such as 40, 42 and 44, which are connected to high voltage sources 46, 48 and 50, thus making it possible to render live a random number of the said electrodes. As the latter have a sector shape on the periphery and the flow is radial and centripetal, it is sufficient for blocking the operation of a sector corresponding to a given electrode, to place the same under an adequate voltage for stopping, as from entry 12, all the particles charged with the opposite sign to that of the polarity chosen for the said electrode.

In other words, each of the sector electrodes 40, 42, 44 etc. functions as an electrostatic trap. If they are all supplied or energized, they stop all the particles, so that none of the latter will be collected on the collecting disk 16. However, if any random one of the electrodes 40, 42, 44, etc. is not energized, i.e. it is left at ground potential, the corresponding angular sector will allow the passage of the charged particles towards the corresponding sector of the plate 16. It is thus possible to obtain deposits on said support disk 16, in accordance with individual sectors and a predetermined sequence. This can be very useful for following in time the evolution of the contamination in a particular ambient, by initiating or starting juxtaposed, radial sectors of the detector.

A description will now be given relative to FIG. 6, which constitutes an improvement to the electrostatic detector according to FIG. 1 and which is arranged so as to permit the collection of all the aerosol particles contained in an atmospheric sample to be examined. For this purpose and prior to the entry into the actual detector, charging takes place of all the aerosol particles contained in the sample to be examined with the aid of charges which all have the same sign. In example 6, this is obtained with the aid of an annular chamber 52 located at the entry 12 of the atmospheric flow to be examined and containing an ionizing source 54 equipped with an equipotential grid 56. The ionizing source 54 can e.g. be an alpha radioactive source and which brings about within the entire annular chamber 52 the creation of positive and negative ion pairs. As a function of the polarizing voltage values chosen for the source 54 and the grid 56, the latter only allowing the passage to the outside towards the air flow to be examined of charges having the same sign and which will then be fixed to the particles contained in the entering air flow. If the polarization of the disk 16 is then of opposite sign to that of said same particles, they will be reliably deposited on said disk 16, where it is then possible to examine them. The satisfactory operation of the means according to FIG. 6 consequently requires that the polarities of the polarizing grid 56 and the conductive disk 16 are opposite.

In other embodiments not shown in the attached drawings, the polarization of all the particles with the aid of charges of the same sign prior to their examination by the detector is carried out with the aid of charged microdots bringing about the ionization by the corona effect, said microdots being distributed over an annular chamber identical to chamber 52 in FIG. 6.

Finally, in the embodiment according to FIG. 7, it is one of the actual disks, namely the disk 16, which emits ionizing radiation. In the means according to FIG. 7, there is generally only a central suction flow Q2 via pipe 8 and the lower conductive disk 18 is simply suspended on the lower part of the case 2 by claws or grips such as 58. In the means according to FIG. 7, it is the electrode 16, which is supported by the solid part 64, which is raised to the high voltage, whereas the collecting electrode 18 is grounded. The electrode 16 raised to high voltage is made from an alpha radioactive material and an electrically insulated polarizing grid 60 is at intermediate equipotential between the high voltage of the electrode 16 and the ground of the electrode 18. This grid 60 has a double function in that it extracts the ions of a single polarity in the region where the aerosols introduced by the annular, lateral slot 12 prior to their suction by the axial tube and it establishes a uniform electric field in said region so that the thus charged aerosols are deposited on the collecting disk 18. The latter must obviously have at least one conductive face and can be made from a random metallic material, or more simply it can be a standard silicon wafer if it is wished to carry out an examination under the a priori very slightly polluted conditions of a white room of the microelectronics industry. The apparatus of FIG. 7 makes it possible to collect all the positive, negative or neutral particles contained in an atmosphere to be examined. However, as it is not possible to control the law according to which the particles are charged within the case 2 under the influence of the alpha source forming the disk 16, the apparatus cannot function in electric mobility spectrometry.

In order to avoid a possible penetration of aerosols into the area where the radioactive source is distributed over the disk 16, in certain cases said zone can be supplied at a low flow rate with filtered gas through the eccentric tube 62 in accordance with the path indicated by the arrows.

It should be noted that the suction diagram used in the embodiment of FIG. 7 is characterized by a single central suction and not by a central suction associated with a peripheral injection and is not bound by the existence of a surface ionization source and can instead be transposed to all the embodiments described hereinbefore.

EXAMPLE OF THE CONSTRUCTION OF ANOTHER MOBILITY SELECTOR

The term mobility selector or differential mobility analyzer means an apparatus able to sort or separate the aerosol particles contained in a given gaseous phase as a function of their electric mobility, which is a well known quantity and whose definition has been given hereinbefore. Such apparatuses already exist in the industry and are used either for producing aerosols with a known electric mobility, or in certain cases aerosols having a perfectly known diameter and often referred to as monodispersed aerosols.

In the hitherto known constructions, the electric mobility selectors have a cylindrical symmetry and the two electrodes present are respectively constituted by two coaxial, hollow, conductive metal cylinders having different diameters. The central cylinder is provided with a circular slot into which are sucked the particles of given electric mobility. This geometry suffers from the disadvantage of not being sufficiently compact for certain applications.

However, by having a mobility selector in accordance with the model diagrammatically shown in FIG. 8, in which it is possible to see the electrostatic detector with its two coaxial disk 16 and 18 and its extraction tube 8, it is possible to solve the problem in a simple and advantageous manner.

Thus, in FIG. 8 it is possible to see the lateral edges of the aforementioned electrostatic detector having two openings, namely an upper opening 70 through which are sucked the aerosols to be analyzed and a lower opening 72 provided with a filter 74 through which is injected the scavenging air extracted by the tube 8.

According to the invention, the lower conductive disk 16 is provided with an annular slot 76 centred on the common axis 78 of the two disks 16 and 18 and through said slot 76 are sucked the particles, whose mean trajectory between points A and B is indicated in dotted line form by line 80 in the drawing. These particles are sucked through the slot 76 due to the fact that their normal impact location in the absence of the said slot 76 would have been the point B located at the distance from the axis 78 equal to the radius of the annular slot 76. In order to bring about said suction, it is possible to use a number of different means without passing outside the scope of the invention. In particular and this is the case in the embodiment shown in FIG. 1, it is possible to use a cylindrical case 82 attached beneath the disk 18 and provided with an e.g. axial tube 84, through which is sucked a flow rate q well below the primary extraction flow rate Q withdrawn through the duct 8. In this way, tube 84 collects all the aerosol particles which have passed through the annular slot 76 and which, by definition, have the same electric mobility.

In order to regulate said electric mobility to the individually desired value, it is possible to act on the two parameters constituted by the flow rate Q on the one hand and the potential difference V applied according to the invention between the two conductive, coaxial disks 16 and 18 on the other.

CONSTRUCTION OF AN APPARATUS FOR OBTAINING A STANDARD SURFACE DEPOSIT

The following example relates to the application of the electrostatic detector to producing an apparatus for obtaining a homogeneous surface particle deposit standard on a disk-like substrate.

A certain number of recent industrial developments and particularly the need to produce in large working areas very high purity atmospheres with respect to the contamination by dust particles (white rooms) have made it increasingly necessary to study the aerosols contained in the atmosphere and consequently to obtain very accurate knowledge on the contamination level of a given atmosphere. For this purpose it is useful to have surface standards, more particularly "contaminated" silicon wafers, which are standards with respect to the size or concentration of particles deposited on a substrate.

Thus, "contaminated" silicon wafers have been artificially produced with the aid of aerosols of monodispersed latex polystyrene microspheres permitting the particle size calibration of the surface deposit analyzers.

The methods used for producing such deposits are not well known and can consequently not be easily used or reproduced.

In other constructions of the same type, particle concentration standards have been produced by etching microscopic points or dots on a substrate, the number of such dots being precisely defined and known by a photolithographic process. It is obvious that this method is difficult to carry out and leads to relatively expensive standards.

Therefore the present example relates to a process making it possible to bring about standard surface contaminations, both as regards size and concentration, whilst guaranteeing a perfectly homogeneous deposit. This process can also be used for the deposition on substrates of particles having a perfectly controlled physicochemical nature for the needs of research and in particular in microelectronics.

The Applicant has found that it was possible to apply the aerosol particle electrostatic detector according to the invention to the obtaining of such a deposit through forming one of the two conductive disks thereof by the substrate on which it is wished to deposit the standard contamination.

With reference to the attached FIG. 9, which shows an electrostatic detector, an explanation will now be given of the physical principle on which said application is based. FIG. 9 shows the detector in a diagrammatic form by its two conductive, coaxial disks 16 and 18 and its suction tube 8 for the extraction flow Q. The entry of the aerosol particles which it is wished to deposit on the lower disk 16 is located on the surface of the disk 18 and is in the form of an annular injection slot 12 through which said particles are sucked. If the gaseous suction flow rate through the annular slot 12 is Q, it is clear that the entrainment gas flow rate required on the open periphery of the two coaxial disks 16 and 18 is equal to Q−q. If Z is the electric mobility of the particles, 2h the distance separating the electrode disk 16 and 18, rA the radial distance from the annular slot 12 to the axis of the system and r the impact radius of a given particle, the theory of the apparatus shows that within the detector on disk 16, the aerosol particles are deposited on a circumference of radius r defined by the following formula:

$$r = \sqrt{r_A^2 - \frac{2\,Qh}{\pi\,ZV}}$$

in which V is the potential difference applied between the circular, coaxial electrodes 16 and 18. In the above formula, if it is considered that in a particular given case, the values of the flow rate Q and the voltage V are fixed, it is clear that it is only as a function of their electric mobility Z that the different particles constituting the aerosol penetrating the detector through the annular slot 12 are distributed in accordance with different radii on the surface of the circular electrode 16. Consequently, if it is wished to displace the deposit of the particles from radius r to radius r+dr, there are only two possibilities, namely either reducing the suction flow rate Q, or increasing the voltage V. As experimentally, the second solution is far easier and in particular more accurate, this is chosen within the scope of the present invention. Thus, by carrying out a scan of the voltage and by passing it continuously through various values, it is possible to obtain a dispersion of the deposit of the aerosol particles on the circular electrode 16 used as a substrate for the future surface standard. However, it is obvious that said voltage V must not vary in a random manner as a function of time, if it is wished to obtain a standard having a homogeneous surface concentration, i.e. having at all points the same number of particles per surface unit. In order to bring about the homogeneity of such a deposit, the voltage V must vary in time according to a particular law which has been determined by the Applicant and which is expressed by the following formula:

$$V = \frac{2h}{Z\left(\frac{\pi r_A^2}{Q} - \frac{N}{S}\,t\right)}$$

in which S is the surface density which it is wished to obtain on the deposition electrode 16, t is the time and N the concentration of particles in the extraction flow Q when V=0.

Moreover, the preceding result cannot be obtained on the basis of any random population of aerosol particles.

Thus, three quantities characterize the particles of any aerosol, namely the electric mobility, the electric charge and the size of each particle. Without wishing to enter into theoretical detail and which is in any case not necessary for understanding and reproducing the means according to the invention, it is pointed out that these three quantities are linked with one another by a relation which can be written in the following way:

$$Z = \frac{peC}{3Z\mu d}$$

in which Z is the electric mobility of a particle, e the elementary charge, p the number of elementary charges of a particle, C a coefficient and d the diameter of each particle. Thus, if at least two of these three quantities are identical for all the particles this is sufficient to ensure that the thus constituted aerosol will lead to a homogeneous surface deposit by applying the above law of the variation of the voltage V as a function of the time.

With reference to FIG. 10 a description will now be given of the basic diagram for the application of the aerosol particle electrostatic detector to the production of a concentration surface standard. FIG. 10 shows the electrostatic detector 87 with its concentric electrode disks 16 and 18 and its annular slot 12 for the access of the aerosols to be dispersed within the detector 87. The complete unit is located within a sealed enclosure 86 supplied by duct 88 with a gaseous flow containing the aerosol particles. The main suction flow Q of the electrostatic detector 87 circulates in the latter and in the enclosure 86 by a pipe 90. It is injected through a filter 92 and discharged to the outside of the enclosure 86 after fulfilling its entrainment function. A pipe 94 makes it possible to extract and discharge to the outside through the filter 96, the excess atmosphere possibly contained in the said enclosure 86.

According to the invention, the aerosol particles entering the enclosure 86 through the duct 88 have predetermined characteristics and in particular the same value for all the particles of two of the three quantities constituted by the electric mobility, the charge and the size. In a particular, but frequently used case, the aerosol is in the form of calibrated latex balls and it is then known that it is easy, by passing the thus formed aerosol through a differential mobility selector, to obtain a population of aerosol particles all having the same electric charge, same size and same electric mobility. This particularly easily realizable case makes it possible to supply duct 88 at the entry of enclosure 86.

By respecting the particular conditions of the injected aerosol and the variation in the potential difference V between the two disks 16 and 18 as a function of time, on the electrode 16 used as the deposition substrate is obtained a homogeneous surface contamination having a value S (in number of particles per surface unit) which is chosen beforehand.

EXAMPLE OF PRODUCING A TOTAL SELECTION DETECTOR FOR PARTICLES HAVING A GRAIN SIZE BELOW A GIVEN THRESHOLD

This example relates to the application of the electrostatic detector to producing an apparatus making it possible to detect or collect all the particles having a grain size below a given threshold. Such an apparatus has numerous possible applications, one of the most important being the study in an atmosphere with aerosols dispersed in the grain size normally inhaled by the respiratory tracts of man, because it is generally assumed that the particles which can be breathed by man and which are liable to pass through the larynx are those having a grain size below 10 micrometers. Therefore this apparatus makes it possible to collect in a random atmosphere all the dust which could be inhaled by a human being present in said atmosphere.

The total selection apparatus combines the principle of grain size selection by inertial separation and a total collection electrostatic detector as defined with reference to FIG. 7.

FIG. 11 diagrammatically shows the construction of the total selection detector. It is possible to see the detector, as described relative to FIG. 7 with its electrodes 16 and 18, the electrode 16 being an ionizing emitter, its equipotential grid 60 and its central suction tube 8 through which is discharged the flow $Q_2$. According to the invention, with said structure has been combined a grain size selection structure by inertial separation and which essentially comprises, in the gas flow entering the apparatus periphery 12 with a rate of $Q_1+Q_2$, an annular slot 98, whose width is approximately 1 mm and through which is sucked into the space between the coaxial electrodes 16 and 18 the atmosphere flow $Q_2$. The remaining fraction $Q_1$ of the flow entering at 12 into the said apparatus and which does not enter the electrostatic detector is directly discharged by another central tube 100.

According to the invention, the slot 98 in combination with the suction flow $Q_2$ passing through it constitutes an inertial grain size selection separator and on the basis of an appropriate choice and the particular circumstances an interruption takes place of the aerosol particles entering the selector at a particular grain size by choosing the size of the annular slot and the flow rate $Q_2$ passing through it.

In a frequently used application, there is an accurate choice of the dimensions of the annular slot 98 and the value for the flow rate $Q_2$, so as to cut off the particles at the aerodynamic diameter of 10 micrometers which, by physical means, brings about the grain size selection which would take place in a human larynx. In this way, all the particles which would be inhaled by said human being enter the slot 98 and are then absorbed and fixed on the collecting plate 18 of the total selection electrostatic detector with a view to a subsequent analysis.

I claim:

1. Electrostatic detector for aerosol particles contained in an atmosphere to be examined, characterized in that it comprises two parallel, spaced, coaxial conductive disks (16, 18) between which is established an electric field raising them to different potentials, each said disk having a center and a peripheral region disposed radially outwardly of, and completely surrounding, said center, and said two disks delimiting a space which extends between said center and said peripheral region of each said disk, fluid delivery means disposed for delivering the atmosphere to be examined to said space at a location adjacent said peripheral regions of said disks, and a central suction tube (8) communicating with said space adjacent said centers of said disks in order to bring about a flow in said space from the peripheral regions of the disks to the suction tube, of at least part of said atmosphere in the form of a stable, centripetal, laminar flow.

2. Electrostatic detector according to claim 1, characterized in that the atmospheric flow rate Q1 to be examined is the differential resultant of the central suction flow rate Q2 and a peripheral injection flow rate $Q_o$ of filtered gas, the latter being regulated to a value below that of the suction flow.

3. Electrostatic detector according to claim 2, characterized in that it is constituted by a flattened circular cylindrical case (2) having two axial pipes, one for injecting a gas (4) into the lower part of the case and the other for extracting the gas (8) in the upper part of said case, the latter being provided on its upper periphery with an annular slot (12) for the entry of the atmosphere to be analyzed and, in its centre, a solid thick disk (14), whose upper face supports one of the two conductive disks (16), the second conductive disk (18) being constituted by the upper cover of the case, the injection gas flow passing round the thick disk after passing through a filter (20) for the purification and uniform distribution of its flow.

4. Electrostatic detector according to claim 2 for collecting aerosol particles having two signs, characterized in that it is constituted by a circular, cylindrical case (26) which, in its diametral plane of symmetry, has an annular, peripheral opening (12) for the suction of the atmospheric flow rate to be examined and, along its circular axis of symmetry and in both the upper and lower parts, on each occasion two concentric pipes (28, 30), the central pipe (30) being used for the suction flow and the outer pipe (28) for the injection flow, the two conductive disks (16, 18) being positioned symmetrically facing on either side of the diametral plane of symmetry and are raised to symmetrical potentials with respect to earth or ground and of opposite signs, each central suction pipe issuing into the space between the two disks by an orifice (40, 42) made in the centre of each of them.

5. Electrostatic detector according to claim 1 for producing an aerosol particle electric mobility spectrometer, characterized in that the intensity of the electric field between the two disks and the radial, laminar flow rate of the atmospheric sample to be examined are chosen so as to obtain fixing dispersed in the form of concentric, annular zones over the disks of at least part of the said particles, the mobility spectrum being deduced by a calculation or by data processing on the basis of the examination of the location and the density of the preceding zones and the grain size of the particles.

6. Electrostatic detector according to claim 1 for producing a collector of the aerosol particles contained in an atmosphere to be examined, characterized in that the part of said atmosphere entering the detector is subject to electric means with the same sign for all the particles constituting the aerosol.

7. Electrostatic detector according to claim 6, characterized in that said electric charging means are located at the entry of the gaseous flow between the two disks and are constituted by an annular chamber (52) containing an ionizing radioactive source (54) and a polarization grid (56) charging the particles with the same sign prior to their entry into the detector.

8. Electrostatic detector according to claim 6, characterized in that the electric charging means for the particles are located at the entry of the gaseous flow between the two disks and are constituted by an annular chamber provided with microdots supplied with high voltage and bringing about ionization by the corona effect.

9. Electrostatic detector according to claim 6, characterized in that the electric charging means for the particles are constituted by one of the two disks (16), which emits ionizing radiation.

10. Electrostatic detector according to claim 1, characterized in that the gas extraction pipe is equipped with a static filter (36) for collecting the neutral aerosol particles possibly contained in the atmosphere to be examined.

11. Electrostatic detector according to claim 3, characterized in that it comprises, at the entry of the annular slot (12) and located in the case, a certain number of sector-like peripheral electrodes (40, 42, 44 etc.), each provided with an electric supply for raising them to an adequate potential for trapping all the particles entering the corresponding sector and consequently allowing the detector to operate by sequential sectors.

12. Electrostatic detector according to claim 1 for producing an electric mobility selector for the particles of an aerosol, characterized in that at least one of the two coaxial, conductive disks (16, 18) is provided with an annular slot (76) centred on the axis common to the two disks in conjunction with means (84) for sucking through said slot particles which would be normally deposited on the disk at the location of said slot if it did not exist.

13. Electrostatic detector according to claim 12, characterized in that the suction means are constituted by a cylindrical case (82), which is connected beneath the disk (16) containing the slot (76) and provided with a suction tube (84) for permitting the selective extraction of particles having the electric mobility corresponding to the radius of the slot (76).

14. Electrostatic detector according to claim 1 for producing an apparatus for obtaining homogeneous surface deposit standards for particles on a disk-like substrate, characterized in that the electrostatic detector, whose substrate constitutes one of the conductive disks, is supplied by an aerosol particle flow having in common the same value for two out of the three quantities constituted by the electric mobility, the charge and the size and in that the potential difference V between the disks of the detector is varied as a function of time during the deposit and in accordance with the law:

$$V = \frac{2h}{Z\left(\frac{\pi r_A^2}{Q} - \frac{N}{S}t\right)}$$

in which:

h is the half-distance between the plates,

Z is the electric mobility common to the particles, rA is the distance from the aerosol injection point to the detector axis, Q is the extraction flow rate of the gaseous phase from the detector, N is the concentration of particles in the extraction flow rate Q, when V=0, S is the surface density of the particles which it is wished to obtain on the collecting disk, t is time.

15. Electrostatic detector with total collection in accordance with claim 9 for producing a total selection detector of all the aerosols having a grain size below a given threshold, characterized in that on the introduction path of the gaseous phase containing the aerosols, said detector has a calibrated annular slot (98) for bringing about, for an appropriate extraction flow, the inertial separation of the particles having a grain size below the selected threshold.

* * * * *